United States Patent
Zhu

(10) Patent No.: US 8,022,080 B2
(45) Date of Patent: Sep. 20, 2011

(54) SMALL MOLECULES WITH ANTIPROTOZOAL ACTIVITY

(75) Inventor: Shuren Zhu, Potomac, MD (US)

(73) Assignee: Radix Pharmaceuticals Inc., Potomac, MD (US)

(*) Notice: Subject to any disclaimer, the term of this patent is extended or adjusted under 35 U.S.C. 154(b) by 377 days.

(21) Appl. No.: 12/454,046

(22) Filed: May 13, 2009

(65) Prior Publication Data

US 2010/0292264 A1    Nov. 18, 2010

(51) Int. Cl.
*A61K 31/44* (2006.01)
(52) U.S. Cl. .......................... 514/280; 514/279
(58) Field of Classification Search ............ 514/280, 514/279
See application file for complete search history.

(56) References Cited

OTHER PUBLICATIONS

Yarnell et al. "Bontanical treatment and prevention of malaria: part 2-selected botanicals." Alternative and complementary therapies, 2004, vol. 10, No. 5, pp. 277-284.*
Uhegbu et al. "Comparative efficacy of crude aqueous extract of *Mangiferea indica, Carca papaya* and sulphadoxine pyrimethamine on mice infested with malaria parasite in vivo," Global Journal of Pure and Applied Sciences, 2005, vol. 11, No. 3, pp. 399-401, CAPLUS Abstrac, AN 2005:728725t.*

* cited by examiner

*Primary Examiner* — Shengjun Wang

(57) ABSTRACT

The present invention provides new chemical compositions with desirable biological activity and toxicity profiles for the enhanced treatment of malaria.

1 Claim, 2 Drawing Sheets

Chemical structure of isolated natural products. (Formula A and Formula B).

Formula A

Formula B

Figure 1. Chemical structure of isolated natural products. (Formula A and Formula B).
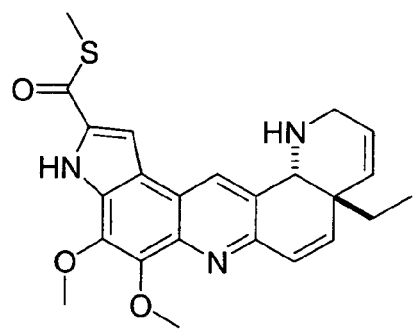
Formula A
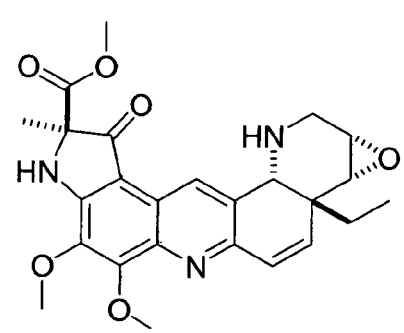
Formula B
Figure 2. Chemical structure of natural product derivatives (Formula I and Formula II).
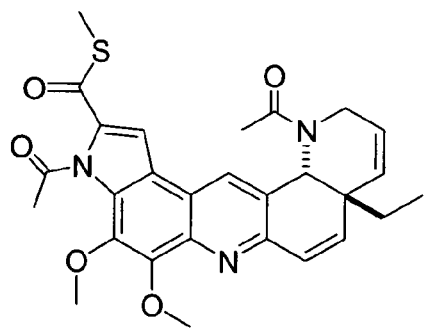
Formula I
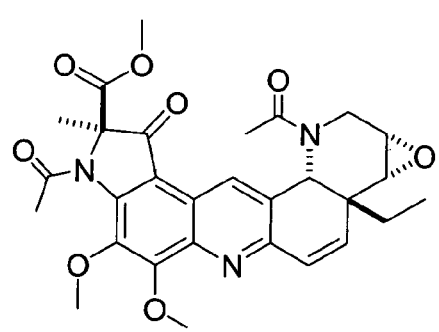
Formula II Figure 3. Synthesis of natural product derivatives Formula I and Formula II.
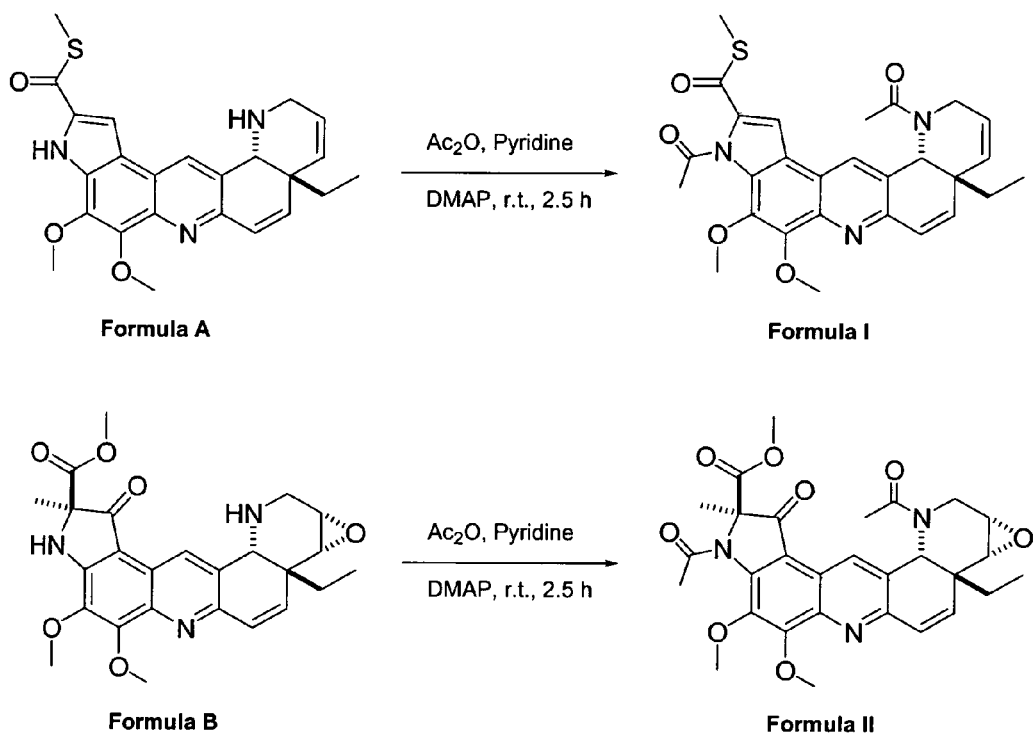

SMALL MOLECULES WITH ANTIPROTOZOAL ACTIVITY

STATEMENT REGARDING FEDERALLY SPONSORED RESEARCH OR DEVELOPMENT

This invention was supported by Public Health Service Grant Number: 1R43AI081308-01 for Radix Pharmaceuticals, Inc. The U.S. Government has a paid-up license in this invention and the right in limited circumstances to require the patent owner to license others on reasonable terms as provided for by the terms of Grant Number: 1R43AI081308-01 awarded by Public Health Service.

CROSS-REFERENCE TO RELATED APPLICATIONS

Not Applicable.

REFERENCE TO SEQUENCE LISTING, A TABLE, OR A COMPUTER PROGRAM LISTING COMPACT DISC APPENDIX

Not Applicable.

FIELD OF INVENTION

The present invention relates to new chemical compositions that are effective for the treatment of malaria.

BACKGROUND OF THE INVENTION

Malaria is the best known protozoal disease, caused by one of four species of the sporazoa type—*Plasmodium falciparum, P. vivax, P. ovale*, and *P. malariae*. It is one of the most common infectious diseases in at least 100 tropical and subtropical countries in Africa, Southeast Asia, and South America. According to WHO, one out of every seventeen people alive today will die from a disease transmitted by the bite of a mosquito. Worldwide, malaria infects 300-600 million people and kills about three million in a year. The increasing prevalence of multiple drug resistant strains of *Plasmodium falciparum* in most malaria endemic areas has significantly reduced the efficacy of current anti-malarial drugs for prophylaxis and treatment of this disease. Although drug resistance is a common problem in the treatment of most microbial infections, malaria and many neoplasms, the impact is more acute for malaria chemotherapy because of the limited number of clinically useful anti-malarial drugs.

Only six prescription drugs are available in the US for treating and/or preventing malaria: Atovaquone/proguanil, Doxycycline, Mefloquine, Primaquine, Chloroquine phosphate, and Hydroxychloroquine sulfate. All of them are discovered more than 40 years ago. Serious side effects are common. Primaquine is the only available causal prophylactics. It has a low therapeutic index. The use of chloroquine is limited because of the worldwide emergence of drug-resistant strains of *P. falciparum* and *P. vivax*. Proguanil has a short half-life and strains of *P. falciparum* resistant to proguanil are common. The newest antimalarial drug Mefloquine was developed in the late 1960s. It is initially reserved by WHO for use in regions where drug resistance to chloroquine is a serious problem. However, problems have arisen with mefloquine use. The cure rate for mefloquine-sulfadoxine-pyrimethamine treatment of *P. falciparum* in Southeast Asia fell from 96% in 1985 to as low as 50% in 1990. Mefloquine can also produce adverse neurological and psychiatric reactions. Artemisinin and its derivatives are currently under development. However, these compounds cannot be used during pregnancy since they have shown fetotoxicity in rodent models. The current generations of artemisinins possess poor efficacy of monotherapy. Artemisinins do not interfere with hepatic stages of parasite development and therefore have no causal prophylactic value.

Therefore, novel medicinal agents are urgently needed to overcome the emergence of resistance and to control an ever-increasing number of epidemics caused by the malaria parasite.

For decades, natural products have been a wellspring of drugs and drug leads. According to a recent survey, 61% of the 877 small-molecule new chemical entities introduced as drugs worldwide during 1981-2002 can be traced to or were inspired by natural products. These include natural products (6%), natural product derivatives (27%), synthetic compounds with natural-product-derived pharmacophores (5%), and synthetic compounds designed on the basis of knowledge gained from a natural product (that is, a natural product mimic; 23%). In certain therapeutic areas, the productivity is higher: 78% of antibacterials and 74% of anticancer compounds are natural products or have been derived from, or inspired by, a natural product.

*Carica papaya* L., a perennial tropical tree, belongs to the family of Caricaceae, and is commonly known as papaya, paw paw, kates, or papaw. It has an erect, branchless trunk with scars from old leaf stems. It is really only a very coarse and robust herb with leaves reaching sometimes nearly 3 feet across. *Carica papaya* L. is widely grown in tropical regions, including Central America, the Amazon region, and the Florida, Hawaii, Puerto Rico of the United States, for its edible fruit known as papaya. The fruit is high in vitamin A and is consumed fresh when ripe while the green fruits are grated in salads or boiled like squash. The green fruit of papaya is the source of the enzyme papain, which is used in meat tenderizers and many other biologically active phytochemicals. The leaves of papaya are divided into several lobes, which radiate like the fingers of the hand. In Suriname's traditional medicine, the boiled green leaves of papaya are used against malaria and as an anthelmintic, the seeds as a vermifuge and tea of the fallen leaves against hypertension. The decoction of the leaves has also been used as a treatment for intestinal parasites.

An ethanol extract of the dried leaves of *Carica papaya* L. exhibited considerable in vitro antimalarial activity to warrant fractionation. On the basis of the initial activity of crude extracts, attention was focused on the bioactivity-guided fractionation of the EtOH extract of the dried leaves, which resulted in the isolation of two new antimalarial natural products, Formula A and Formula B. Their chemical structures are shown in FIG. 1. Formula A, bearing two secondary amine moieties, was converted into the corresponding di-acetamide compound Formula I. Formula B, also bearing two secondary amine moieties, was converted into the corresponding di-acetamide compound Formula II. The chemical structures of the natural product derivatives, Formula I and Formula II, are shown in FIG. 2. The synthesis route is shown in FIG. 3.

Two *Plasmodium falciparum* malaria parasite clones, W2 (chloroquine resistant) and D6 (chloroquine sensitive), were utilized for in vitro efficacy testing. All new compounds were also tested for toxicity against human adult liver epithelial cells (THLE-3). Natural products Formula A and Formula B showed modest inhibitory activity against both chloroquine sensitive malaria strain (D-6) and chloroquine resistant malaria strain (W-2). The two derivative compounds Formula I and Formula II showed equally potent inhibitory activity against both chloroquine sensitive malaria strain (D-6) and chloroquine resistant malaria strain (W-2). The $IC_{50}$'s (concentration of compound that affords 50% of inhibition) were superior to the positive controls, chloroquine and mefloquine. Noticeably, these compounds also showed much reduced toxicity.

In mice models, both Formula I and Formula II have shown excellent blood schizonticidal activity and oral prophylactic activity.

The present invention relates to new, more active and less toxic natural product derivatives for the treatment of malaria.

SUMMARY OF THE INVENTION

The present invention provides new chemical compositions and methods of isolation and synthesis and using as antimalarial agents thereof. The present invention relates to improvements in the chemotherapy of malaria through isolation and chemical synthesis of new compounds with desirable biological activity and toxicity profiles for enhanced treatment.

Accordingly, this invention provides new chemical compound Formula I, whose chemical structure is shown in FIG. 2.

Formula I

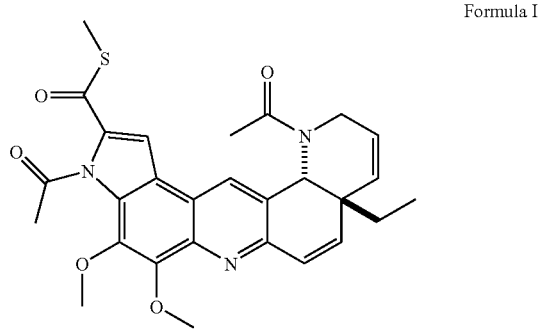

The invention also provides new chemical compound Formula II, whose chemical structure is shown in FIG. 2.

Formula II

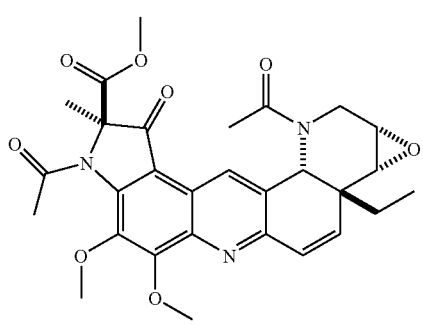

Two natural product compounds were isolated and purified from the plant *Carica papaya* L. and their derivatives were synthesized. In vitro and in vivo antimalarial activities were evaluated. Natural products Formula A and Formula B showed modest inhibitory activity against both chloroquine sensitive and chloroquine resistant malaria strains. The two natural product derivatives Formula I and Formula II showed equally effective and potent inhibitory activity against both chloroquine sensitive and chloroquine resistant malaria strains. It was observed that these derivative compounds possessed potent antimalarial activity in mouse malaria models. Hence, the present invention comprises the use of new chemical compounds for the enhanced treatment of malarial infections.

BRIEF DESCRIPTION OF THE DRAWINGS

These and other features, aspects, and advantages of the present invention will become better understood with regard to the following description, appended claims, and accompanying drawings wherein:

FIG. 1 shows the structures of isolated natural product compounds Formula A and Formula B.

FIG. 2 shows the structures of newly synthesized derivative compounds Formula I and Formula II.

FIG. 3 shows the chemical synthesis route.

DETAILED DESCRIPTION OF THE INVENTION

As mentioned earlier, the invention provides the following compounds: Formula I and Formula II, as shown in FIG. 2.

The invention is inclusive of the compounds described herein in any of their pharmaceutically acceptable forms, including isomers such as diastereomers and enantiomers, salts, solvates, polymorphs, and the like.

Isolation of Natural Products Formula A and Formula B.

General Experimental Procedures. Melting points (uncorrected) were recorded on an Electrothermal 9100 instrument. Optical rotations were measured using a JASCO DIP-370 digital polarimeter in MeOH at ambient temperature. UV spectra were obtained in MeOH, using a Hewlett-Packard 8452A spectrophotometer. IR spectra were taken as KBr disks on an Ati Mattson (Genesis Series) FTIR spectrophotometer. The NMR spectra were recorded on a Bruker Avance DRX-500 instrument at 500 MHz ($^1$H) and 125 MHz ($^{13}$C) in appropriate deuteriated solvent. Multiplicity determinations (DEPT) and 2D NMR spectra (COSY, HMQC, HMBC) were run using standard Bruker pulse programs. The HRMS were obtained by direct injection using Bruker Bioapex-FTMS with electrospray ionization (ESI). TLC was carried out on Silica gel F254 plates, with appropriate solvent system. For flash column chromatography, Silica gel from J. T. Baker (40 μm flash) was used. Centrifugal preparative TLC (using a Chromatotron instrument, Harrison Research Inc. model 8924) was carried out on 4 mm Silica gel GF Chromatotron rotors (Analtech, Inc.), with the appropriate solvent system. The isolated compounds were visualized using UV light, followed by spraying with anisaldehyde/$H_2SO_4$ reagent. All solvents are recycled when possible.

Extraction and Isolation. The powdered air-dried leaves of *Carica papaya* L. (20 kg) were extracted by percolation with 95% EtOH (35 L×3). The combined extracts were evaporated separately under reduced pressure and then freeze-dried to yield a thick paste (2.2 kg). A portion of the paste (1.1 kg) was extracted with 0.05 N hydrochloric acid; the acid solution was extracted with chloroform. The chloroform was recycled and the residue from the chloroform solution was discarded. The aqueous phase was then made basic with sodium carbonate and extracted exhaustively with chloroform. The combined $CHCl_3$ fraction was dried over anhydrous $Na_2SO_4$ and evaporated under a vacuum to yield 530 g of residue. The $CHCl_3$ residue (530 g) was flash chromatographed on silica gel, using $CHCl_3$-MeOH—$NH_4OH$ (96.75/3.0/0.25) as eluant to afford a light yellow solid (36 g). This was crystallized from $CHCl_3$-MeOH by slow evaporation at room temperature to give Formula A as pale yellow needles (29 g). Further elution with CHCl₃-MeOH—NH₄OH (93.75/6.0/0.25) followed by concentration yielded a yellow solid (32 g). Crystallization from CHCl₃-MeOH by slow evaporation at room temperature gave Formula B as pale yellow needles (25 g). Yield: Formula A: 0.29% from dried leaves; Formula B: 0.25% from dried leaves. The structures of Formula A and Formula B are elucidated by MS (HRESIMS), IR, UV, and NMR (2D COSY, HMQC, HMBC) methods. Both compounds possess satisfactory spectroscopic and analytical data.

Synthesis of Derivative Compounds Formula I and Formula II.

Synthesis of Formula I. Formula A (29 g) was dissolved in 50 mL of pyridine. 4-Dimethylaminopyridine (DMAP, 300 mg) and acetic anhydride (Ac₂O, 20.4 g) was then added in. The resulting solution was stirred at room temperature for 12 h. Pyridine were removed under reduced pressure in a rotary evaporator. The residue was partitioned between ethyl acetate (500 mL) and water (500 mL). The organic layer was separated, washed with brine, and concentrated. Crystallization from CHCl₃ by slow evaporation at room temperature gave Formula I as white needles (31 g). Yield: 90%.

Synthesis of Formula II. Formula B (25 g) was dissolved in 45 mL of pyridine. 4-Dimethylaminopyridine (DMAP, 220 mg) and acetic anhydride (Ac₂O, 16.4 g) was then added in. The resulting solution was stirred at room temperature for 12 h. Pyridine were removed under reduced pressure in a rotary evaporator. The residue was partitioned between ethyl acetate (450 mL) and water (450 mL). The organic layer was separated, washed with brine, and concentrated. Crystallization from CHCl₃ by slow evaporation at room temperature gave Formula I as white needles (26 g). Yield: 88%.

The structures of Formula I and Formula II are elucidated by MS (HRESIMS), IR, UV, and NMR (2D COSY, HMQC, HMBC) methods. Both compounds possess satisfactory spectroscopic and analytical data.

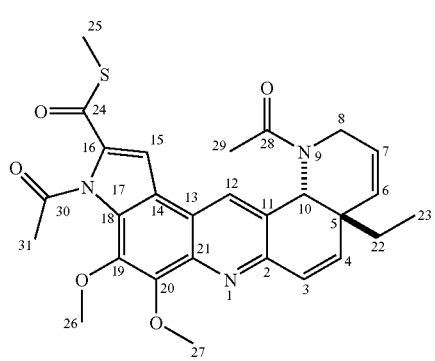

Formula I

Formula I (hydrochloride salt): white needles, melting point 181-182° C.; $[\alpha]_D$ −31.6° (c 0.25, MeOH); UV (MeOH) $\lambda_{max}$ (log ε) 236 (4.05), 280 (3.45), 325 (2.70), 360 (3.35) nm; IR (KBr) $\nu_{max}$ 3050, 3035, 2990-2855, 1675, 1665, 1650, 1615, 1585, 1465, 1375, 1360, 1330, 1295, 1245, 1130, 1090, 862, 835 cm⁻¹. ¹H NMR (CD₃OD) $\delta_H$ 7.61 (1H, s, H-12), 7.38 (1H, s, H-15), 6.51 (1H, d, J=9.2 Hz, H-3), 5.91 (1H, d, J=9.2 Hz, H-4), 5.77 (1H, ddd, J=8.9, 6.5, 4.2 Hz, H-7), 5.72 (1H, d, J=8.9 Hz, H-6), 4.25 (1H, s, H-10), 3.83 (3H, s, H-26), 3.75 (3H, s, H-27), 3.51 (1H, dd, J=13.8, 6.5 Hz, H$_a$-8), 3.44 (1H, dd, J=13.8, 4.2 Hz, H$_b$-8), 2.27 (3H, s, H-25), 2.20 (3H, s, H-31), 2.07 (3H, s, H-29), 1.33 (2H, q, J=6.9 Hz, H-22), 1.02 (3H, t, J=6.9 Hz, H-23). ¹³C NMR (CD₃OD) $\delta_C$ 177.0 (C, C-24), 171.2 (C, C-30), 169.4 (C, C-28), 160.5 (C, C-2), 138.8 (C, C-21), 138.5 (C, C-16), 137.8 (C, C-19), 136.7 (CH, C-4), 133.8 (C, C-20), 133.6 (CH, C-6), 133.5 (CH, C-12), 127.3 (CH, C-3), 125.3 (C, C-11), 123.8 (C, C-13), 122.3 (CH, C-7), 120.2 (C, C-14), 118.6 (C, C-18), 116.0 (CH, C-15), 63.6 (CH, C-10), 57.1 (CH₃, C-26), 56.3 (CH₃, C-27), 46.5 (CH₂, C-8), 40.4 (C, C-5), 25.7 (CH₂, C-22), 17.1 (CH₃, C-29), 16.4 (CH₃, C-31), 15.1 (CH₃, C-25), 9.8 (CH₃, C-23). HRESIMS m/z 542.1732 [M+Na]⁺ (calcd for C₂₈H₂₉N₃NaO₅S⁺, 542.1726) (100%). Anal. Calcd for C₂₈H₂₉N₃O₅S.HCl: C, 60.48; H, 5.44; Cl, 6.38; N, 7.56; S, 5.77. Found: C, 60.53; H, 5.40; Cl, 6.44; N, 7.61; S, 5.70.

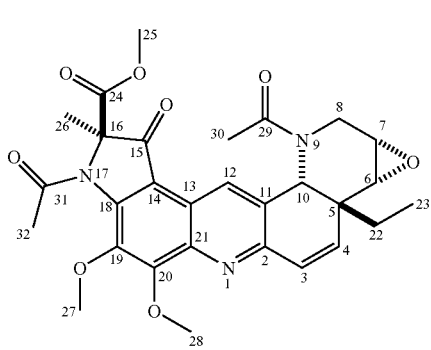

Formula II

Formula II (hydrochloride salt): white needles, melting point 185-186° C.; $[\alpha]_D$ +19.8° (c 0.22, MeOH); UV (MeOH) $\lambda_{max}$ (log ε) 244 (4.28), 276 (3.19), 334 (2.69), 373 (3.25) nm; IR (KBr) $\nu_{max}$ 3025, 2995-2860, 1740, 1680, 1675, 1660, 1655, 1620, 1580, 1460, 1370, 1365, 1325, 1290, 1250, 1125, 1080, 865, 825 cm⁻¹. ¹H NMR (CD₃OD) $\delta_H$ 8.38 (1H, s, H-12), 6.56 (1H, d, J=9.0 Hz, H-3), 5.94 (1H, d, J=9.0 Hz, H-4), 4.05 (1H, s, H-10), 3.77 (3H, s, H-27), 3.73 (3H, s, H-28), 3.69 (3H, s, H-25), 2.89 (1H, dd, J=13.4, 7.3 Hz, H$_a$-8), 2.82 (1H, dd, J=13.4, 4.1 Hz, H$_b$-8), 2.76 (1H, ddd, J=7.3, 4.7, 4.1 Hz, H-7), 2.59 (1H, d, J=4.7 Hz, H-6), 2.15 (3H, s, H-32), 2.09 (3H, s, H-30), 1.75 (3H, s, H-26), 1.31 (2H, q, J=7.1 Hz, H-22), 0.99 (3H, t, J=7.1 Hz, H-23). ¹³C NMR (CD₃OD) $\delta_C$ 197.6 (C, C-15), 172.4 (C, C-31), 172.0 (C, C-24), 166.5 (C, C-29), 157.3 (C, C-2), 138.3 (C, C-18), 135.3 (CH, C-4), 134.7 (C, C-20), 132.3 (C, C-19), 130.8 (C, C-21), 130.4 (CH, C-3), 128.3 (CH, C-12), 126.6 (C, C-11), 120.4 (C, C-13), 107.1 (C, C-14), 82.1 (C, C-16), 64.0 (CH, C-6), 57.2 (CH, C-7), 56.9 (CH₃, C-27), 56.4 (CH₃, C-28), 56.1 (CH, C-10), 50.4 (CH₃, C-25), 47.0 (CH₂, C-8), 39.4 (C, C-5), 21.7 (CH₂, C-22), 16.9 (CH₃, C-30), 16.1 (CH₃, C-32), 15.7 (CH₃, C-26), 9.5 (CH₃, C-23). HRESIMS m/z 572.1998 [M+Na]⁺ (calcd for C₂₉H₃₁N₃NaO₈⁺, 572.2009) (100%). Anal. Calcd for C₂₉H₃₁N₃O₈.HCl: C, 59.44; H, 5.50; Cl, 6.05; N, 7.17. Found: C, 59.52; H, 5.47; Cl, 6.12; N, 7.11.

It is understood that while a compound of the general structural formulas herein may exhibit the phenomenon of tautomerism, the structural formulas within this specification expressly depict only one of the possible tautomeric forms. It is therefore to be understood that the structural formulas herein are intended to represent any tautomeric form of the depicted compound and is not to be limited merely to a specific compound form depicted by the structural formulas.

It is also understood that the structural formulas are intended to represent any configurational form of the depicted compound and is not to be limited merely to a specific compound form depicted by the structural formulas.

Additionally, the compounds of the invention include pharmaceutically acceptable salts, multimeric forms, active metabolites, precursors and salts of such metabolites of the compounds of the present invention.

The compound of the present invention is a base, the desired pharmaceutically acceptable salt may be prepared by any suitable method available in the art, for example, treatment of the free base with an inorganic acid, such as hydrochloric acid, hydrobromic acid, sulfuric acid, nitric acid, phosphoric acid and the like, or with an organic acid, such as acetic acid, maleic acid, succinic acid, mandelic acid, fumaric acid, malonic acid, pyrvic acid, oxalic acid, glycolic acid, salicylic acid, a pyranosidyl acid, such as glucuronic acid or galacturonic acid, an .alpha.-hydroxy acid, such as citric acid or tartaric acid, an amino acid, such as aspartic acid or glutamic acid, an aromatic acid, such as benzoic acid or cinnamic acid, a sulfonic acid, such as p-toluenesulfonic acid or ethanesulfonic acid, or the like.

The compound of the present invention are solids, it is understood by those skilled in the art that the compound of the present invention and salts may exist in different crystal or polymorphic forms, all of which are intended to be within the scope of the present invention and specified structural formulas.

The compounds of the present invention in accordance with the present invention are useful in the treatment of malaria and diseases and disorders associated with malaria or a *Plasmodium* parasite.

Antimalarial Activity

For in vitro efficacy evaluation, Formula I and Formula II were tested against two *P. falciparum* malaria parasite clones: W2 (chloroquine resistant) and D6 (chloroquine sensitive). For in vitro toxicological studies, the following cell line was chosen: human adult liver epithelial cells (THLE-3). THLE-3 cells express phenotypic characteristics of normal adult liver epithelial cells and constitute a valuable model for pharmacotoxicological studies. The $IC_{50}$ values (50% inhibitory concentrations) were summarized in Table 1.

TABLE 1

In Vitro Activity Against Malarial Parasites and Cell Lines [$IC_{50}$ (ng/ml)]

| Test Compounds | D6 Strain | W2 Strain | THLE-3 | Selectivity[a] |
|---|---|---|---|---|
| Formula A | 11.3 | 10.7 | 17900 | 1584 |
| Formula B | 8.6 | 9.4 | 16500 | 1919 |
| Formula I | 0.32 | 0.29 | 17100 | $5.3 \times 10^4$ |
| Formula II | 0.21 | 0.23 | 15400 | $7.3 \times 10^4$ |
| Chloroquine | 6.3 | 108 | 2920 | 463 |
| Mefloquine | 3.4 | 5.6 | 2700 | 794 |

[a]Selectivity is calculated as $IC_{50}$ (THLE-3)/$IC_{50}$ (D6).

Both natural product Formula A and Formula B possess modest antimalarial activity. Their corresponding derivatives, Formula I and Formula II, possess antimalarial activity superior to the commonly used antimalarial drugs, chloroquine and mefloquine and have shown potency against both chloroquine sensitive malarial strain (D-6) and chloroquine resistant malarial strain (W-2). Noticeably, all new compounds were much less toxic than chloroquine and mefloquine.

The blood schizonticidal activity of these new natural product derivatives Formula I and Formula II was determined as described herein (Table 2).

TABLE 2

Antimalarial Activity of Natural Product Derivatives Formula I and Formula II: Blood schizontocidal activity against *P. berghei* in mice.

| | Mice surviving 60 days/Mice infected and treated Oral Dose, mg/kg, day; (Total dose, mg/kg) | | | | |
|---|---|---|---|---|---|
| Compound | 0.25 (0.75) | 1.0 (3.0) | 4.0 (12) | 16 (48) | 64 (192) |
| Chloroquine | 0/7 | 0/7 | 2/7 | 4/7 | 0/7 |
| Formula I | 7/7 | 7/7 | 7/7 | 7/7 | 7/7 |
| Formula II | 7/7 | 7/7 | 7/7 | 7/7 | 7/7 |
| Control | 0/7 | | | | |

Both compounds (Formula I and Formula II) are very active and much less toxic (no mice showed toxicity at the highest dose tested). These compounds had also shown excellent activity by the subcutaneous route of administration [J. Med. Chem., 25, 1094(1982) M. P. LaMontagne et al.] (See Table 3).

TABLE 3

Suppressive Antimalarial Activity of New Natural Product Derivatives Formula I and Formula II: Blood schizontocidal activity against *P. berghei* in mice (subcutaneously as a single dose).

| | Mice surviving 60 days/Mice infected and treated Dose, mg/kg | | | | | | | |
|---|---|---|---|---|---|---|---|---|
| Compounds | 1 | 2 | 4 | 8 | 16 | 32 | 64 | 128 |
| Formula I | 4/5 | 5/5 | 5/5 | 5/5 | 5/5 | 5/5 | 5/5 | 5/5 |
| Formula II | 4/5 | 5/5 | 5/5 | 5/5 | 5/5 | 5/5 | 5/5 | 5/5 |
| Control | 0/5 | | | | | | | |

Mice were treated with a single dose of the compound administered subcutaneously 72 h after infection. Number of cures is the number of mice surviving, out of five, 60 days postinfection.

Compounds were tested for oral prophylactic activity. Mice treated with a single dose of 0.5 mg/kg of Formula I or Formula II within the period of 2 days pre-infection through 2 days post-infection were completely protected from malaria. Data were summarized in Table 4 and Table 5.

TABLE 4

Prophylactic Anti-Malarial Activity of Formula I.

| | Mice infected and treated/Mice surviving day 60 dose, mg/kg | | | |
|---|---|---|---|---|
| Day of Treatment | 0.5 | 2 | 8 | 32 |
| −2 | 5/5 | 5/5 | 5/5 | 5/5 |
| −1 | 5/5 | 5/5 | 5/5 | 5/5 |
| 1 | 5/5 | 5/5 | 5/5 | 5/5 |
| 2 | 5/5 | 5/5 | 5/5 | 5/5 |
| Controls | 0/5 | | | |

TABLE 5

Prophylactic Anti-Malarial Activity of Formula II.

| Day of Treatment | Mice infected and treated/Mice surviving day 60 dose, mg/kg | | | |
|---|---|---|---|---|
| | 0.5 | 2 | 8 | 32 |
| −2 | 5/5 | 5/5 | 5/5 | 5/5 |
| −1 | 5/5 | 5/5 | 5/5 | 5/5 |
| 1 | 5/5 | 5/5 | 5/5 | 5/5 |
| 2 | 5/5 | 5/5 | 5/5 | 5/5 |
| Controls | 0/5 | | | |

The present invention, hence, relates to the finding that some new natural product derivative compounds (Formula I and Formula II) have significantly greater activity and less toxicity in the treatment of malaria. The present invention relates to new chemical compositions and also to the use of these compositions as pharmaceuticals when combined with an acceptable pharmaceutical carrier in the treatment of malaria.

Administration of the compounds of the invention may be parenteral, oral, intravenous, intramuscular, subcutaneous, intrapleural, intrathecal, intraperitoneal, aerosol or transdermal administration to achieve the desirable antimalarial effect. These drugs may be administered as the free base form or in the form of a pharmaceutically acceptable acid addition salt wherein the acid addition salt may be either organic or inorganic in nature. Suitable inorganic acids for salt formation include but are not restricted to: phosphoric acid, hydrochloric acid or sulfuric acid. Suitable organic acids for the formation of salts may include but are not restricted to: succinic acid, citric acid, fumaric acid or isothionic acid. When administered orally, the compounds of the invention may be in the form of tablets (single or multilayer, coated or uncoated) capsules or dragees. These oral formulations may be admixed with a solid excipient such as lactose, sucrose, starch, microcrystalline cellulose, magnesium sterate, or talc. When parenteral administration may be indicated, an aqueous solution or an oleaginous formulation of the agent may be employed. Aqueous solutions can be prepared in water or physiological saline, either with or without buffers. Oleaginous formulation may be made in natural oils such as peanut oil or olive oil, for example. The actual dosage amount administered can be determined by physical and physiological factors such as body weight, severity of condition, and idiopathy of the subject.

Biological Testing Procedures

In Vitro Anti-Malarial Activity Evaluation

Two *P. falciparum* malaria parasite clones, W2 and D6, from Malaria Research and Reference Reagent Resource Center (MR4), were utilized in susceptibility testing. The W2 clone is susceptible to mefloquine but resistant to chloroquine, sulfadoxine, pyrimethamine, and quinine, whereas the D6 clone is naturally resistant to mefloquine but susceptible to chloroquine, sulfadoxine, pyrimethamine and quinine. Test compounds were initially dissolved in DMSO and diluted 400 fold in RPMI 1640 culture medium supplemented with 25 mM Hepes, 32 mM $NaHCO_3$ and 10% Albumax I (Gibco, N.Y.). These solutions were subsequently serially diluted two-fold with a Beckman Biomek® 1000 Robot (Fullerton, Calif.) over 11 different concentrations. The parasites were exposed to serial dilutions of each compound for 48 hrs and incubated at 37° C. with 5% $O_2$, 5% $CO_2$ and 90% $N_2$ prior to the addition of [$^3$H]hypoxanthine. After a further incubation of 18 hrs, parasite DNA was harvested from each microtiter well using Packard Filtermate™ 196 Harvester (Meriden, Conn.) onto glass filters. Uptake of [$^3$H]hypoxanthine was measured with a Packard TopCount Liquid Scintillation Counter (Packard Instrument Co.). Concentration-response data was analyzed using a non-linear regression logistic dose response model and the $IC_{50}$ values (50% inhibitory concentrations) for each compound were calculated.

In Vitro Toxicity Evaluation

Human adult liver epithelial cells (THLE-3) was maintained in tissue culture flasks in Waymouth's medium (Gibco, N.Y.) supplemented with 10% fetal bovine serum. Toxicity tests were performed in 96-well tissue culture plates using the protein-binding dye Sulforhodamine B. Test compounds were serially diluted and added to empty wells of the 96-well plate. THLE-3 cells in their culture medium were immediately seeded into the wells. Solvent blanks (no compound) were run in each test. After 72 hours under culture conditions cells were fixed to the plate by layering 50% TCA (4° C.) over the growth media in each well to produce a final TCA concentration of 10%. After incubating for one hour at 4° C., cultures were washed five times with tap water and left airdried. Wells were stained for 30 min. with 0.4% (w/v) SRB in 1% acetic acid and washed four times with 1% acetic acid. Cultures were left air-dried and bound dye was solubilized with 10 mM Tris base (pH 10.5) for 15 min. on a gyratory shaker at room temperature. A Spectra MAX Plus Microtiter Plate Reader (Molecular Devices, Menlo Park, Calif.) was used to measure the optical density at wavelengths of 490-530 nm. The 50% cell growth inhibitory concentration ($IC_{50}$) value was derived from the dose-response curve.

Blood Schizontocidal Test in Animals

Drugs were mixed in 0.5% hydroxycellulose 0.1% Tween 80 and administered orally b.i.d. on days 3, 4 and 5 postinfection. CD-1 male or female mice, 5 weeks of age, were infected with $5.\text{times}.10.\text{sup}.4$ parasitized erythrocytes of *Plasmodium berghei* KBG-173 mm strain. Blood films were taken on day +6 and weekly thereafter until day +60. Parasitemias were calculated and SD90 value (dose suppressing 90% of the parasites in treated groups compared with the infected non-treated controls) on day +6 postinfection. Mortality data was tabulated for 60 days at which time all mice surviving that were blood film negative were considered cured.

Compounds were tested at three dose levels, 4, 1, and 0.25 mg/kg body weight per day. The activity of these compounds were compared with the untreated control. In untreated controls, death occurs within 8-9 days. Compounds which are effective against *Plasmodium berghei* infection increase the mean survival time of the infected animals when compared with the untreated controls. Mice that survive after thirty days and are free of parasites in blood are considered cured.

Efficacy of the drug is determined by the number of cures at the end of a 30 day period and the increase in mean survival time over the control (.DELTA.MST). The effect of the test drugs also could be determined by the reduction of the parasitemia (percentage of the red blood cells detected with the parasites) over the untreated control on day 6, one day after the treatment is completed. Both these methods yield virtually identical results. If the dose of test compounds are inadequate, after initial clearance, residual parasites will multiply and relapses will occur within thirty days.

Prophylactic Test in Animals

Drugs were mixed in 0.5% hydroxycellulose 0.1% Tween 80 and administered orally b.i.d. either on day 5, 4, 3, 2, or 1 prior to the infection or 1 or 2 days postinfection. CD-I male or female mice, 5 weeks of age, were infected with $5.\text{times}.10.\text{sup}.4$ parasitized erythrocytes of *Plasmodium berghei* KBG-173 mm strain. Blood films were taken on day +6 and weekly thereafter until day +30. Mortality data was tabulated for 30 days at which time all mice surviving that were blood film negative were considered cured.

Unless defined otherwise, all technical and scientific terms used herein have the same meaning as commonly understood by one of ordinary skill in the art to which this invention belongs. Although any methods and materials similar or equivalent to those described can be used in the practice of testing of the present invention, the preferred methods and materials are described herein.

It is understood that the examples and embodiments described herein are for illustrative purposes only and the various modifications or changes in light thereof will be suggested to persons skilled in the art and are to be included within the spirit and purview of this application and scope of the appended claims.

What is claimed is:
1. A method for the treatment of malaria comprising administering to a subject a therapeutically effective amount of a compound having the Formula I:
Formula I
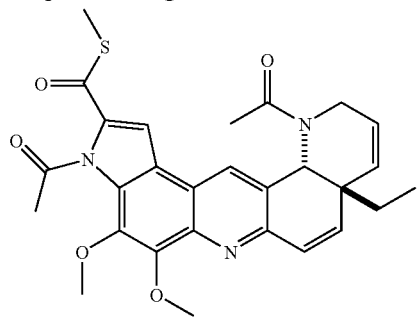
Or a compound having the Formula II:
Formula II
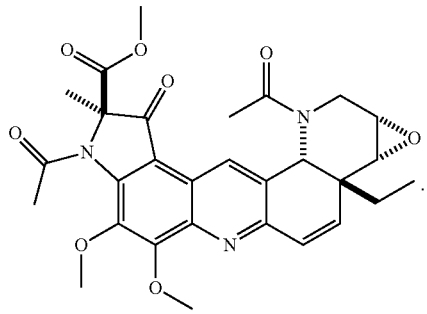
* * * * *